United States Patent [19]

Watson et al.

[11] 4,446,864
[45] May 8, 1984

[54] EMERGENCY VENTILATION TUBE

[76] Inventors: Robert L. Watson, 14312 Piccadilly Rd., Silver Spring, Md. 20906; Robert L. Rayburn, 495 North Hills Dr., Salt Lake City, Utah 84103

[21] Appl. No.: 281,066

[22] Filed: Jul. 7, 1981

Related U.S. Application Data

[63] Continuation-in-part of Ser. No. 168,193, Jul. 10, 1980, abandoned.

[51] Int. Cl.³ .............................................. A61M 16/00
[52] U.S. Cl. ............................. 128/207.14; 128/202.28
[58] Field of Search ...................... 128/207.14, 207.15, 128/349 B, 200.26, 202.28

[56] References Cited

U.S. PATENT DOCUMENTS

| | | | |
|---|---|---|---|
| 3,087,493 | 4/1963 | Schessow | 128/207.15 |
| 3,683,908 | 8/1972 | Michael et al. | 128/207.15 |
| 3,874,377 | 4/1975 | Davidson | 128/207.15 |
| 4,090,518 | 5/1978 | Elam | 128/207.15 |
| 4,155,365 | 3/1979 | Boslau | 128/207.15 |
| 4,231,365 | 11/1980 | Scarberry | 128/207.15 |
| 4,334,534 | 6/1982 | Ozaki | 128/207.15 |
| 4,351,328 | 9/1982 | Bodai | 128/202.16 |

FOREIGN PATENT DOCUMENTS

| | | | |
|---|---|---|---|
| 68597 | 8/1969 | Fed. Rep. of Germany | 128/207.15 |
| 1505607 | 12/1967 | France | 128/349 B |

OTHER PUBLICATIONS

An Unusual Complication of Esophageal Obturator Airway (EOA), Berkebile et al., Anesthesiology 57:414-415, 1982.

*Primary Examiner*—Henry J. Recla
*Attorney, Agent, or Firm*—Roylance, Abrams, Berdo & Goodman

[57] ABSTRACT

An emergency esophageal ventilating airway includes coaxial tubular members insertable through a patient's mouth and into the esophagus. The coaxial tubes are attached to a coupling which is inserted into a standard face mask. The longer, inner, one of the tubes extends into the lower esophagus and has an inflatable occluding cuff at its inner or lower end while the outer end extends through the coupling and mask to the atmosphere providing a clear venting passage from the stomach. The outer tube has holes lying near the laryngeal region and communicates, through chambers in the coupling, with a ventilating gas supply. A second embodiment includes tubes of equal length in concentric relationship, the cuff being on the outer tube. In the second embodiment, the inner tube is distensible so that, when relaxed, maximum air flow volume is available. The inner tube expands to permit passage of an NG tube.

14 Claims, 12 Drawing Figures

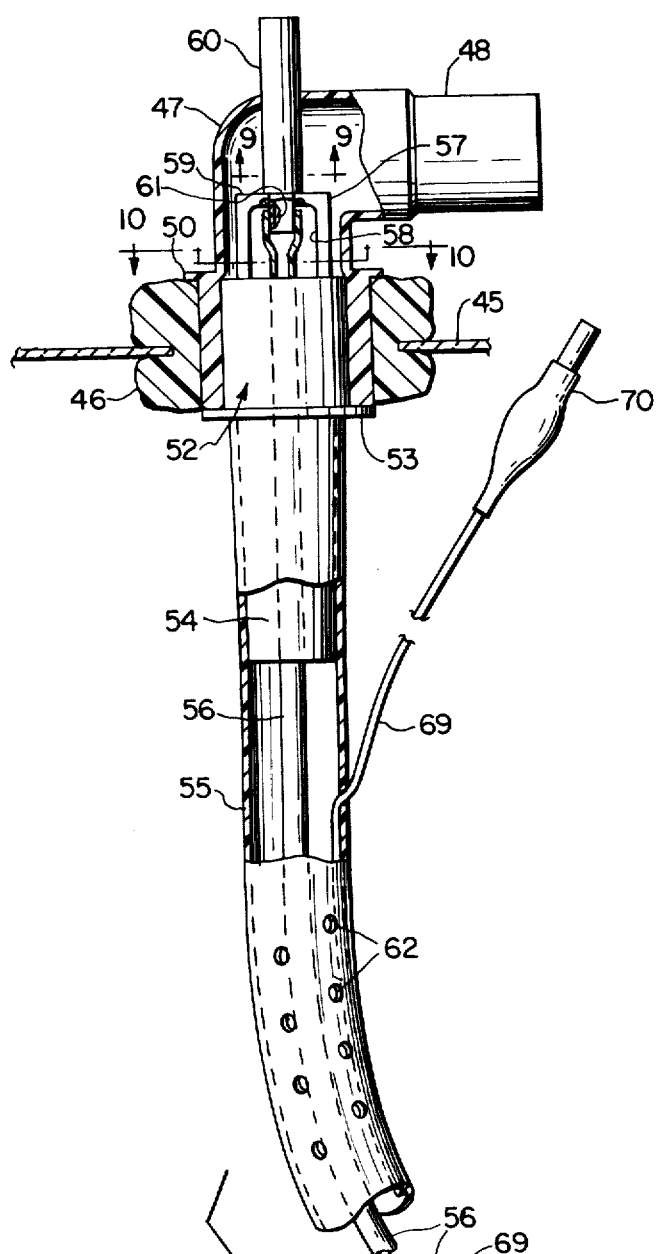
FIG. 9
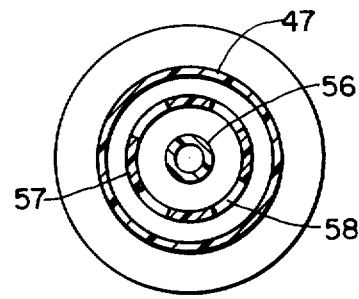
FIG. 10
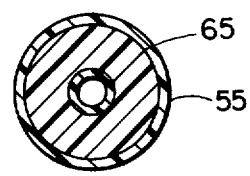
FIG. 11
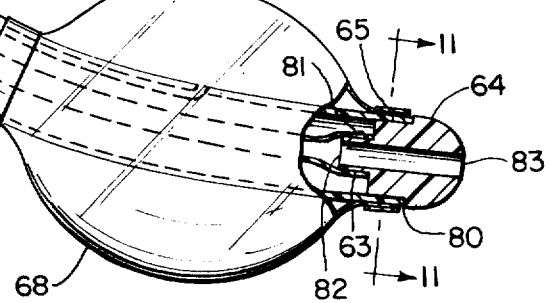
FIG. 8

EMERGENCY VENTILATION TUBE

This application is a continuation-in-part of application Ser. No. 168,193, filed July 10, 1980 and now abandoned, by the same inventors.

This invention relates to an emergency ventilating apparatus and, more specifically, to a combined pharyngeal air-way and esophageal tube primarily for emergency medical use.

BACKGROUND OF THE INVENTION

There are numerous circumstances in which a patient cannot breathe for himself due to trauma, shock or other conditions. It is then necessary to force air or oxygen into and out of the patient's lungs. In such cases, a paramedical person is often faced with the need to accomplish this before or during transportation to a medical center.

It is not sufficient, however, to simply place a mask coupled to an airbag or oxygen supply over the patient's mouth, because the forced-in gas can inflate the stomach and cause material to regurgitate from the stomach and enter the lungs, a very hazardous and life-threatening condition. The mask alone is also insufficient in many cases because the tissues in the mouth and pharyneal area are quite often collapsed, partly or totally blocking the air passage, which is frequently not obviated by standard oral pharyngeal airways.

It is therefore desirable to intubate the trachea with an endotracheal tube (with a cuff in older children and adults) and to ventilate the lungs directly. Unfortunately, the skill to successfully perform endotracheal intubation under the conditions of an emergency is frequently lacking in paramedical personnel, and therefore an easier and more reliable device for securing the airway is necessary. However, there has been no device available which is safely and reliably usable under a variety of conditions to provide the necessary ventilation. Examples of devices previously developed for related purposes are found in the following U.S. Pat. Nos.

3,848,604 Harantuncian et al
3,905,361 Hewson et al
4,090,518 Elam
4,093,484 Harrison et al
4,100,246 Frisch
4,114,625 Onat
4,166,468 Haynie However, each of these has shortcomings which prevent them from fully satisfying all the needs of an emergency ventilating apparatus.

BRIEF SUMMARY OF THE INVENTION

Accordingly, an object of the invention is to provide a device which concurrently provides a clear passage from the lower esophagus and stomach to the ambient atmosphere to prevent stomach distention and regurgitation, provides a passage from a ventilating means to the glottis or larynx region for inflation of the lungs, and occludes the esophagus between the stomach and the hypopharynx to prevent any possible regurgitation from entering the lungs.

A further object is to provide a device which is adapted to be received in a standard face mask, thereby eliminating the need for a special mask.

BRIEF DESCRIPTION OF THE INVENTION

Briefly described, the invention includes a combined pharyngeal airway and esophageal tube comprising a first, distensible inner tube dimensioned to be received in a patient's esophagus and to extend from the lower esophogus to a location outside of the mouth, a second tube having an inner diameter larger than the outer diameter of said first tube, said second tube substantially concentrically surrounding a portion of said first tube and being dimensioned to extend from a location adjacent the patient's mouth to an inner location beyond the hypopharynx, said second tube terminating and being joined to the exterior of said first tube at said inner location, an expandable and collapsible occluding means surrounding said first tube near the end thereof to be positioned in the lower esophagus for preventing passage of fluids outside of said first tube to and from the stomach, means for actuating said occluding means, means in said second tube defining radial passages through the walls thereof for admitting gas into the laryngeal region, and a coupling receivable through a face mask, said coupling having means defining a chamber for conducting ventilating gas to the interior of said second tube, said chamber being joinable at one end to said second tube and at the other end to a source of ventilating gas, and tube guide means within said chamber for receiving said inner tube and for conducting said inner tube through said coupling such that the outer distal end thereof is open to ambient atmosphere.

In order that the manner in which the foregoing and other objects are attained in accordance with the invention can be understood in detail, a particularly advantageous embodiment thereof will be described with reference to the accompanying drawings, which form a part of this specification, and wherein:

FIG. 2 is a perspective side elevation of the first embodiment of the apparatus in accordance with the invention;

FIG. 3 is a transverse sectional view along line 3—3 of FIG. 2;

FIG. 4 is a transverse section view along line 4—4 of FIG. 2;

FIG. 9 is a transverse sectional view along line 9—9 of FIG. 8;

FIG. 10 is a transverse sectional view along line 10—10 of FIG. 8;

FIG. 11 is a transverse sectional view along line 11—11 of FIG. 8; and

DETAILED DISCUSSION OF THE DRAWINGS

Figure 1:
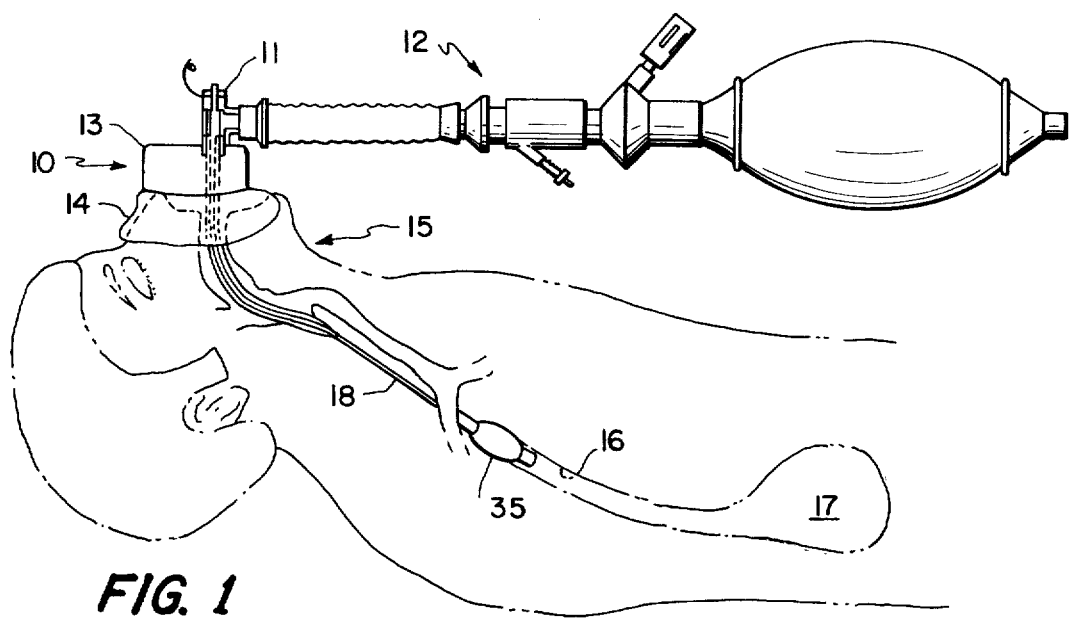
FIG. 1 is a schematic side elevation of a first embodiment of an apparatus in accordance with the invention, illustrated in use with a patient and in conjunction with a source of ventilating gas.

FIG. 1 is included to illustrate an embodiment of the present invention in a typical use thereof and illustrates the general locations of components relative to the patient. As shown therein, a conventional face mask, indicated generally at 10, of the type commonly used for the application of anesthesia, receives the upper portion of the device of the present invention which includes a coupling 11, one portion of which is dimensioned to fit through the standard opening in the mask. A lateral fitting of the coupling is connectable to a source of ventilating gas. In FIG. 1, that lateral fitting is shown connected to a partial re-breathing system indicated generally at 12. The system 12 forms no part of the present invention and will not be further described herein, but it will be recognized that it can be replaced by a oxygen supply or other suitable source of ventilating gas. The mask itself which, as indicated above, is standard, includes a relatively rigid portion 13 and a portion 14 which is flexible, or has flexible edges, to adapt in air-sealing relationship to the face of the patient 15.

Tubes connected to coupling 11, as will be described in somewhat greater detail, extend through the patient's mouth and esophagus, the inner end of the tube extending to the lower portion of the esophagus 16. It will be observed that the tube extends close to, but stops short of, the patient's stomach 17. The tube 18 which extends into the esophagus is provided with an occluding device 19 which will also be further described.

Turning now to FIGS. 2–6, which show the apparatus of the present invention in somewhat greater detail, it will be seen that the coupling 11 includes an upper portion 20 and a lower portion 21, upper portion 20 having a generally cylindrical body defining an interior chamber 22 and a transversely extending fitting 23 which is adapted to be coupled to the ventilating gas source. The upper wall of portion 20 is provided with an opening 24, and the lower outer diameter 25a of portion 20 is dimensioned to pass through the ventilating hole of a standard face mask and is, therefore, 22 mm in diameter. An annular flange 25 limits the extent of insertion of the coupling into the face mask.

Figure 5:
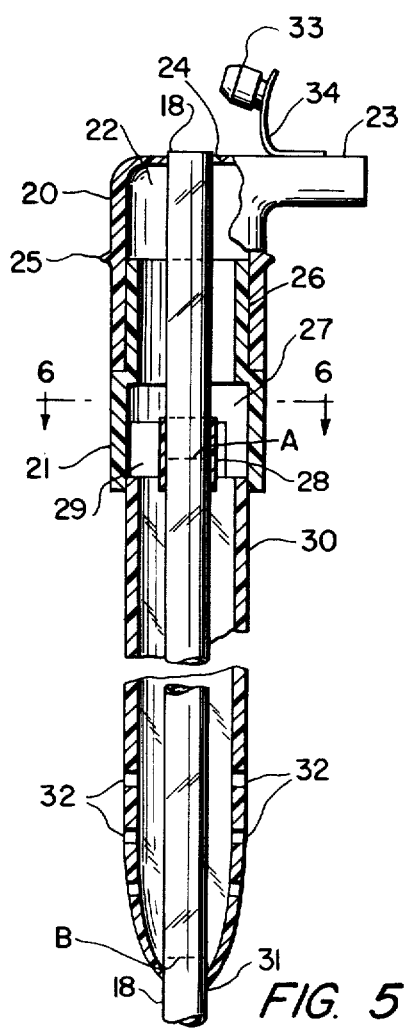
FIG. 5 is a partial side elevation, in partial section, of the upper portion of the apparatus of FIG. 2.
Figure 6:
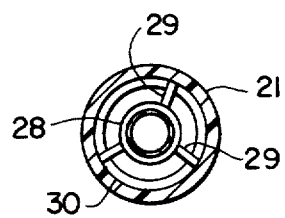
FIG. 6 is a transverse sectional view along line 6—6 of FIG. 5.

The lower portion 21 has a larger portion which is also 22 mm in diameter and an upper, reduced diamter portion 26 which is sufficiently smaller in diameter so as to fit within chamber 22 of the upper portion. When joined, the two portions present an exterior surface of uniform diameter as indicated in FIG. 5.

The lower portion 21 is provided with a tube guide 28 which comprises a relatively short section of hollow, cylindrical tubing having an inner diameter substantially equal to the diameter of opening 24. Tube guide 28 is centrally supported within portion 21, near the lower end thereof, by radially inwardly extended webs 29 which are joined to the inner surface of member 21, thereby supporting the tube guide but leaving the major portion of the interior open for the passage of gas.

The coupling structure thus described is joined to a tubing arrangement including a first, inner tube 18 and a larger diameter, outer tube 30. The outer diameter of tube 30 is substantially equal to the inner diameter of the lower portion 21, and the lower extent of webs 29 is recessed inwardly from the lower end of the lower portion, thereby permitting the upper end of tube 30 to be inserted therein as illustrated in FIG. 5. The inner tube 18 extends through tube guide 28 and extends upwardly through opening 24 at the top of portion 20.

At the lower end of portion 30, that portion is joined to the exterior of inner tube 18 as indicated at 31, which juncture can be formed by welding or by a double-extrusion process. A coupling arrangement can also be used, as will be described in FIG. 7. Tube 30 is provided with a plurality of radially extending openings 32 which permit the passage of gas into and out of the interior of portion 30.

At this stage, it wil be recognized that a continuous passage exists from transversely extending fitting 23 through chamber 22, through chamber 27 in the lower portion of coupling 11, past webs 29 and around tube guide 28, into the interior of outer tube 30 through openings 32. The weld or other attachment at 31 prevents continuous delivery of gas beyond that point, except around the enxterior of the entire structure.

Similarly, it will be recognized that a fluid path exists through inner tube 18 from its open end above opening 24 to the other end of the tube, and that no communication exists between the interior of tube 18 and the interior of any other portions mentioned including coupling 11 and tube 30.

At the upper end of the coupling, a plug 33 is attached to the exterior of fitting 23 on portion 20 of coupling 11 by a flexible web 34 so that the plug can be inserted in the opening 24. With the plug inserted, adaptor 20 can be inserted into a standard face mask without the pharyngeal/esophageal tube breathing device and adaptor 20 can then be connected to a standard ventilating bag through 23 for resuscitation of the patient in the traditional manner.

As seen in FIG. 2, the lower end of tube 18 is provided with an occluding device 19 which is in the form of an inflatable cuff. Inflatable cuffs of this type are well known in endotrachial tubes and similar devices and are not, per se, novel. Cuff 19 is provided with an inflating tube 36 which is of quite small diameter and which is provided at its end with a conventional unidirectionally valved connector 37 of a type attachable to a syringe. Tube 36 is attached to, or formed as a part of, tube 18 and extends along the length thereof at least up to the point of connection 31, from which point it can follow a separate path. The precise path for the inflating tube is of relatively small significance. Although not shown in FIG. 3, two or more independently inflatable cuffs can be provided in which case each cuff would have its own tube 36. As it is well known in this art, when a syringe is connected to connector 37 and operated to force air through tube 36, the cuff is inflated. One structural relationship of tubes 18 and 36 is illustrated in the sectional view of FIG. 3.

Figure 7:
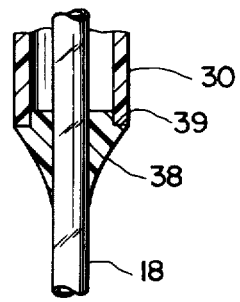
FIG. 7 is a fragmentary side elevation of a portion of an apparatus in accordance with the invention, showing a further embodiment thereof.
Figure 8:
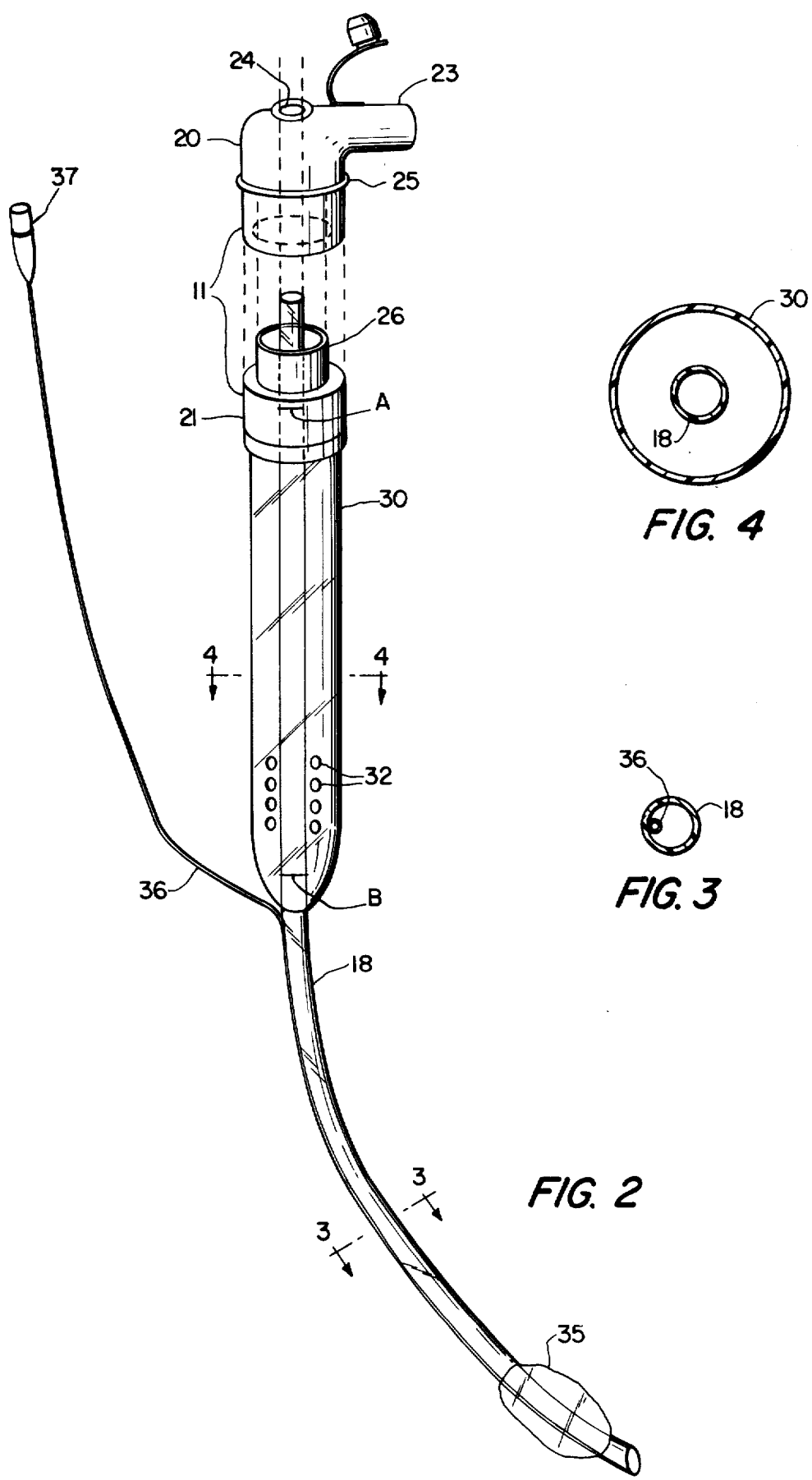
FIG. 8 is a foreshortened side elevation of a preferred embodiment of the invention, partly cut away and partly in section.

An alternative arrangement for the connection at the region of 31 is illustrated in FIG. 7, the fragmentary sectional view thereof showing tube 18 and surrounding concentric tube 30, the embodiment of FIG. 7 also having generally conical connection member 38 which has an inner bore to receive tube 18. Connection member 38 is fixedly attached to tube 18 and is provided with an annular shoulder 39 which receives the end of outer tube 30. The components can be welded or adhered to each other to form a fluidtight connection.

As previously indicated, the endotrachial tube elbow adaptor 20 or coupling device 11 has an outer diameter 25a of 22 mm which permits it to pass through the ventilating hole of a standard face mask such that flange 25 comes to rest at the outer surface of the mask. The inner diameter of upper portion 20 of the elbow adaptor accepts the reduced diameter portion 26 of the lower portion, which has a diameter of 15 mm. The lower portion can thus be regarded as a coaxial tube adaptor.

When the elbow adaptor portion 20 of the coupling 11 is fitted through the ventilating hole of the standard face mask or anesthesia mask, and when the coaxial tube adaptor 21 is inserted into the inside of the elbow adaptor, the proximal portion of the inner tube 18 of the coaxial tube structure is pushed through opening 24. The other end of tube 18 is then inserted through the patient's mouth and tube 18, being relatively stiff, is forced into the patient's esophagus such that the outer tube comes to lie in the hypopharynx area near the patient's glottis and larynx. The assembly is inserted until the face mask fits flush in a tight manner against the patient's face, and it is important to note that the mask covers both the mouth and nose of the patient. With that arrangement, a continuous path exists between the ambient atmosphere through the inner tube and into the lower esophagus below the inflatable cuff, this path being completely separate from the ventilating passage extending from the transversely extending portion of the elbow adaptor 23 through chambers 22 and 27, through outer tube 30 and openings 32.

When a standard self-inflating bag, oxygen powered resuscitator, or any other ventilating device, is attached to the end of the elbow adaptor 20 ventilating port through fitting 23, air or oxygen can be exchanged by forcing the gas through the ventilating path described, leading to openings 32 which lie adjacent the glottis or larynx in the patient's hypopharynx.

A tight fit of the mask against the face prevents ventilating gas from escaping from the pharynx and the inflated cuff or balloon 19, inflated to the point where it is flush against the inner walls of the esophagus, largely prevents ventilating gas from being forced into the stomach.

When ventilating pressure is released or discontinued on the ventilating gas source, exhaled gas or air from the trachea, larynx and glottis passes into the hypopharyngeal area through the outer tube holes 32 and then through the outer tube 30, the coupling 11 and back to the ventilating device through the appropriate valves provided.

Although syringe inflation of the cuff 19 through the tube and connector 36 and 37 occludes the lower esophagus and helps prevent ventilating air or gas from passing into the stomach, some ventilating gas will unavoidably leak through, and if not vented, may distend the stomach. The coaxial tube arrangement allows any ventilating gas which does leak beyond the cuff toward the stomach to be vented directly to the atmosphere, thus preventing such distention. Also, the continuous passage of the inner tube from the lower esophagus to the atmosphere allows a stomach tube of the type referred to as a naso-gastric (NG) tube to be passed for stomach evacuation but permits safe ventilation to be continued concurrently through the outer tube of the coaxial arrangement.

FIGS. 8-11 show a modified and preferred form of an apparatus in accordance with the invention for use with a mask 45, only a portion of which is shown. A standard resuscitating face mask, as shown in FIG. 1 such as but not limited to those manufactured by Ohio Medical Products Co. or the J. H. Emerson Co. can be used. Such masks normally have a central opening with a resilient annular grommet 46.

The apparatus of FIGS. 8-11 is specifically designed to deal with a related set of problems which cannot be solved by prior art devices. These problems are based on the facts that (a) the human pharynx and esophagus are limited in size, placing a constraint on the size of an object which can be inserted therein; (b) it is desirable and, in many cases, necessary to be able to establish at least two and sometimes more separate and mutually isolated passageways into the body through the mouth, pharynx and esophagus; and (c) a flow path having a substantial cross sectional area must be maintained for adequate air or oxygen flow during ventilation.

As will be seen, these facts lead to problems which sometimes conflict. If, as is quite often the case, the patient has a quantity of food in his stomach, that material must be evacuated at some stage during ventilation of his lungs. The ventilation cannot wait until after evacuation, nor can ventilation be interrupted for evacuation. A large NG tube can be used for evacuation, but if a large NG tube was to be coaxially passed through the tube 30 in the structure of FIGS. 1-7 in the position of tube 18, the remaining annulus between tubes 18 and 30 would be too small in cross section to permit adequate air flow for at least the initial stages of ventilation. The size of tube 30 cannot be increased because of the anatomical constraints discussed above.

The solution to this problem, as provided by the embodiment of FIGS. 8-11, is to provide a breathing air passage which is, in a sense, variable by providing an interior passage including a distensible tube through which an NG tube can be passed.

The apparatus is molded in one piece and includes the elbow 47, an end 48 to mate with the breathing air supply, and a sleeve 49 which fits through mask grommet 46, penetration being limited by a flange 50. Sleeve 49 receives a coupling fitting indicated generally at 52 the exterior of one end of which is cylindrical and hollow and is dimensioned to be received within sleeve 49 of fitting 47, insertion being limited by a flange 53.

The other end of coupling fitting 52 is a hollow tapered sleeve 54 which is inserted into a tube 55 which is functionally similar to tube 30 in the embodiment of FIG. 2. The taper permits tube 55 to be tightly attached to sleeve 54, expanding the tube slightly during assembly. This connection can also be cemented.

The upper end of fitting 52 includes a support structure for an interior venting tube 56 and comprises a cylindrical portion 57 of smaller diameter than the interior of sleeve 49, portion 57 having four slots 58 therethrough to form a cage-like structure permiting the free flow of gas between the interior and exterior thereof as best seen in FIG. 10. The upper end of portion 57 has radially inwardly extending arms 59 leading to and supporting a tubular section 60 the upwardly extending portion of which is dimensioned to fit through an opening in the top of fitting 47.

Coaxial with section 60 is a downwardly extending portion 61 which is relatively short. The interior bore through 60 and 61 is dimensioned to pass a large NG tube having an OD of, e.g., 4 mm. Attached to portion 61 is one end of a flexible distensible tube 56 which passes, in a generally coaxial relationship, through tube 55. Tube 56 has an inner diameter which is normally somewhat smaller than the bore through portions 60 and 61, but the tube is sufficiently resilient so that, when an NG tube is inserted therein, tute 56 readily enlarges to permit passage of the NG tube. As will be recognized, this permits the annular space between tubes 55 and 56 to be as large as possible during the time when maximum ventilation is needed, the annulus cross-section being reduced only while the NG tube is present.

The intermediate portion of tube 55 is provided with holes 62 through which air or oxygen can pass into the hypopharyngeal region. Tube 55 is substantially uniform in diameter and the lower distal end thereof is closed by a plug 64 which has a reduced diameter portion 65 dimensioned to tightly fit within tube 55 as best seen in FIG. 11. The enlarged outer portion of plug 64 is rounded to prevent tracheal or esophageal damage during insertion. Plug 64 has a central opening 83 through which the lower end of an NG tube can be passed. In addition, the inner end of portion 64 has a short tubular extension 63 to which the lower end of tube 56 is firmly attached, at junction 81 in FIG. 8. Extension 63, like portion 61, has an outer diameter greater than the normal or relaxed ID of tube 56, but the tube can be stretched to go over the extension. In either case, adhesive can also be used to secure the ends of tube 56.

Figure 12:
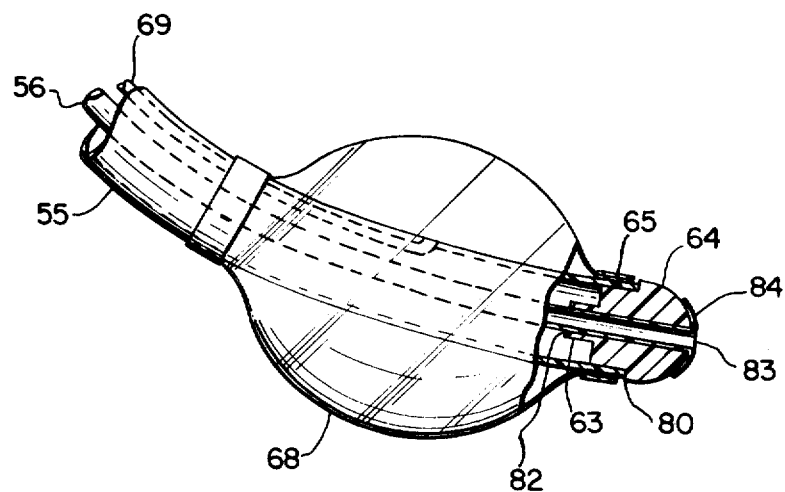
FIG. 12 is a partial sectional view of a further embodiment of a portion of the apparatus of FIGS. 8-11.

FIG. 12 shows another embodiment permitting the passage of inner distensible tube 56 through first aperture 82 of plug 64 and out through second aperature 83 sy ehivh point 84 the distensible tube is flattened and attached with or without adhesive to the rounded outer portion of plug 64. This outer attachment of distensible tube 56 to plug 64 may also be at junction 80 of tube 55 to plug 64 allowing continuity of inner and outer tubes.

An inflatable cuff 68 surrounds tube 55 near the distal end, the function of cuff 68 being the same as cuff 19 in the previously described embodiment. A small tube 69 extends along tube 55, preferably on the interior, from cuff 68 to a valve 70 connectable to a syringe (not shown) by which the cuff can be selectively inflated or deflated in a conventional manner.

As will be recognized, two separate and independent passages are formed by the structure (in addition to the cuff-inflating passage), one being through inner tube 56 between the end plug 64 near the stomach and the upper end in section 60 which is open to the atmosphere. That upper end can, of course, be selectively closed by a plug or cap like that shown in FIG. 2.

The second passage is from the supply of breathable oxygen or other gas connected to portion 48 of fitting 47, through openings 58 in portion 57 to the interior volume inside of tube 55 and outside of tube 56, and through holes 62 into the patient's hypopharynx and thence to lungs. These two passages are isolated from each other when cuff 68 is inflated to seal off the esophagus.

The embodiment of FIGS. 1-7 can also be modified and improved to permit its use with a gastric tube for stomach evacuation. Because of the relatively limp nature of the material used for flexible, distensible tube 56, if that tube material were simply substituted for tube 18 it would not possess sufficient rigidity or stiffness to allow the physician to push it to the lower esophagus. However, it is possible to construct the upper portion of tube 18 above the phantom line A (FIG. 5) and the lower portion of tube 18 below line B of relatively stiff tubing having an inner diameter greater than 4 mm, and to then replace the portion between A and B with a smaller diameter distensible tube, joined at A and B as in the embodiment of FIGS. 8-11 or in any other convenient fashion.

While certain advantageous embodiments have been chosen to illustrate the invention it will be understood by those skilled in the art that various changes and modifications can be made therein without departing from the scope of the invention as defined in the appended claims.

What is claimed is:

1. A combined pharyngeal airway and esophageal tube apparatus for use in combination with a standard face mask of a type which covers both the nasal passages and mouth of a patient, comprising a first, inner tube dimensioned to be received in a patient's esophagus and to extend from a first end adjacent the lower esophagus to a second end adjacent a location outside of the mouth;

a second, outer tube having an inner diameter larger than the outer diameter of said first tube, said second tube generally coaxially surrounding at least a portion of said first tube along the entire length of said second tube and being dimensioned to extend from a first end located adjacent the patient's mouth to a second end located at an inner location beyond the hypopharynx, said second tube terminating and being joined to the exterior of said first tube at said inner location, that portion of said first inner tube within said second, outer tube normally being of a small diameter to maximize the volume between said tubes and being distensible and collapsible to permit passage of a naso-gastric tube larger than said first tube therethrough;

an expandable and collapsible occluding means surrounding at least said first tube near the end thereof which is to be positioned in the lower esophagus for preventing passage of fluids outside of said first tube to and from the stomach;

means for actuating said occluding means;

means in said second tube defining radial passages through the walls thereof for admitting gas into the laryngeal region; and coupling means for mounting said tubes in a standard face mask covering a patient's nasal passages and mouth, said coupling means having first and second open ends and a chamber therein fluidly connecting said first and second open ends, said first open end of said coupling means being connected to said first end of said second tube, said second open end of said coupling means including a laterally opening ventilating port connectable to a ventilating gas source for conducting ventilating gas to the interior of said second tube, said first tube extending into said chamber and through a sidewall of said coupling means to the exterior thereof, said coupling means maintaining said first and second tubes in coaxial relationship.

2. An apparatus according to claim 1 wherein said coupling means further includes tube guide means within said chamber for receiving said inner tube and for conducting said inner tube coaxially through said coupling means and said second tube such that the outer distal end of said inner tube is open to ambient atmosphere, thereby permitting concurrent venting or evacuation of the lower esophagus through the inner tube and ventilation of the lungs through the annular space between said inner and second tubes.

3. An apparatus according to claim 2 wherein said occluding means includes an inflatable cuff surrounding said first tube;

and wherein said means for actuating includes a third tube extending from and communicating with said cuff, and a connector attached to said third tube, said connector being connectable to a syringe for injecting air into said cuff for inflation.

4. An apparatus according to claim 1 wherein said first tube has a blunt plug on an end thereof remote from said coupling means.

5. A combined pharyngeal airway and esophageal tube apparatus, comprising a standard face mask of a type which covers both the nasal passages and mouth of a patient and closely fits the patient's face and which has a central opening;

a first, inner tube dimensioned to be received in a patient's esophagus and to extend from a first end adjacent the lower esophagus to a second end adjacent a location outside of the mouth;

a second, outer tube having an inner diameter larger than the outer diameter of said first tube, said second tube substantially concentrically surrounding a portion of said first tube along the entire length of said second tube and being dimensioned to extend from a first end located adjacent the patient's mouth to a second end located at an inner location adjacent the inner end of said inner tube, said second tube terminating with the interior thereof being joined to the exterior of said first tube at said inner location, that portion of said first inner tube within said second, outer tube normally being of a small diameter to maximize the volume between said tubes and being distensible and collapsible to permit passage of a nasogastric tube larger than said first tube therethrough;

an expandable and collapsible occluding means surrounding said second tube near the end thereof to be positioned in the lower esophagus for preventing passage of fluids outside of said first tube to and from the stomach;

means for actuating said occluding means;

means in said second tube defining radial passages through the walls thereof for admitting gas into the laryngeal region; and coupling means for mounting said tubes in said central opening of said face mask, said coupling means having first and second open ends and a chamber therein fluidly connecting said first and second open ends, said first open end of said coupling means being connected to said first end of said second tube, said second open end of said coupling means including a laterally opening ventilating port connectable to a ventilating gas source for conducting ventilating gas to the interior of said second tube, said first tube extending into said chamber and through a sidewall of said coupling means to the exterior thereof, said coupling means maintaining said first and second tubes in coaxial relationship.

6. An apparatus according to claim 5 wherein said coupling means further includes tube guide means within said chamber for receiving said inner tube and for conducting said inner tube coaxially through said coupling means and said second tube such that the outer distal end of said inner tube is open to ambient atmosphere, thereby permitting concurrent venting of the lower esophagus through the inner tube and ventilation of the lungs through the annular space between said inner and second tubes.

7. An apparatus according to claim 6 wherein said occluding means includes an inflatable cuff surrounding said second tube;

and wherein said means for actuating includes a third tube extending from and communicating with said cuff, and a connector attached to said third tube, said connector being connectable to a syringe for injecting air into said cuff for inflation.

8. An apparatus according to claim 4 where said second tube is sealed to an outer surface of said plug; and said plug closes an end of the interior of said second tube.

9. An apparatus according to claim 8 wherein said first tube is sealed to said plug within said second tube.

10. An apparatus according to claim 8 wherein said first tube extends through said plug.

11. An apparatus according to claim 5 wherein said first tube has a blunt plug on an end thereof remote from said coupling means.

12. An apparatus according to claim 11 where said second tube is sealed to an outer surface of said plug; and said plug closes an end of the interior of said second tube.

13. An apparatus according to claim 12 wherein said first tube is sealed to said plug within said second tube.

14. An apparatus according to claim 12 wherein said first tube extends through said plug.

* * * * *